Aug. 23, 1932. E. H. MANN Plant Pat. 20
YELLOW ROSE
Filed Feb. 29, 1932
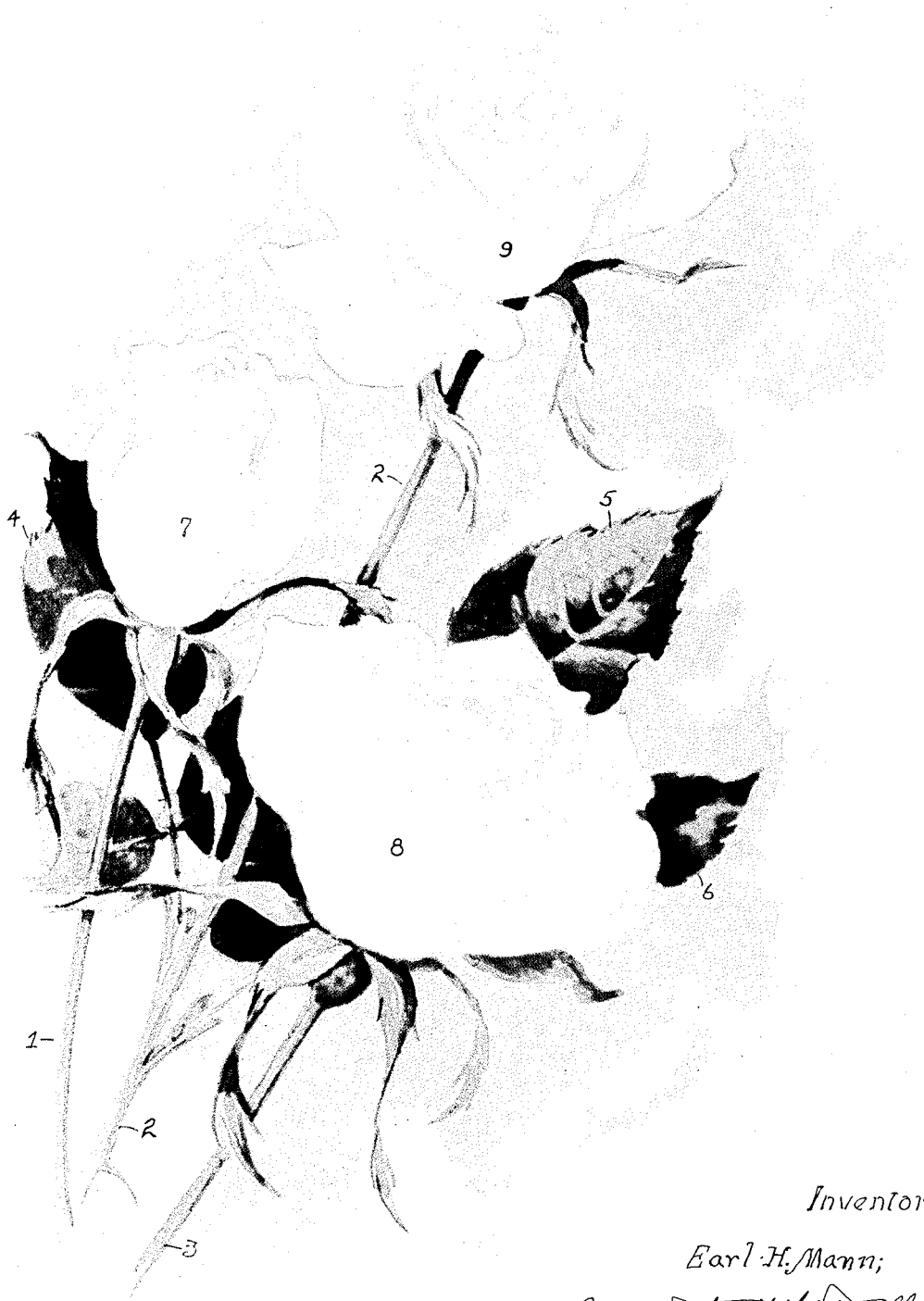
Inventor:
Earl H. Mann;
By Robert W. Landle,
Attorney.

Patented Aug. 23, 1932

Plant Pat. 20

UNITED STATES PATENT OFFICE

EARL H. MANN, OF RICHMOND, INDIANA, ASSIGNOR TO E. G. HILL COMPANY, OF RICHMOND, INDIANA, A CORPORATION OF INDIANA

YELLOW ROSE

Application filed February 29, 1932. Serial No. 595,875.

This invention relates to the production of a new and distinct variety of rose, which is unique in character delectable in appearance, asexually produced, and whose characteristics have been permanently fixed, whereby it may be continuously reproduced without retrogradation.

Broadly stated, the objects which I have attained, in the development of my new rose, is the production of a rose which is particularly attractive in its orientation and coloraturе, and which is predominantly of a rich golden yellow color.

More specifically stated, the objects which have been attained, and incorporated in this product, is a new and distinct variety of rose, the same being quickly recognizable by its rich golden yellow bloom, its unusually large and more pointed buds than that of its parent plant; emitting a maximum of fragrance of a highly delicate and pleasing character; and producing stems of unusually strong and vigorous growth.

Other objects and particular advantages of my new production will suggest themselves in the course of the following description, and that which is new will be correlated in the appended claim which terminates this specification.

A picturization of my new rose is shown in the accompanying painting, forming a part of this specification, wherein is clearly visualized my rose in its natural colors and other new and novel characteristics which have developed therein.

In said painting, numerals 1, 2 and 3, denote the stems,

Numerals 4, 5 and 6 denote the chlorophyl leaves, which diverge from said stems.

And 7, 8 and 9 denote the bloom, in various stages of development.

Numeral 7 denotes a bud just starting to open out; numeral 8 denotes a partly developed rose; and numeral 9 denotes a full blown rose, that is a fully developed bloom.

My new rose was produced from a sport, originating from the variety commonly known as "Talisman," of the class known as a hybrid-tea rose, possessing free blooming qualities.

Immediately after its development said sport was then scientifically and asexually reproduced until its particular characteristics have become permanently fixed, whereby its new and novel features form a variety distinctively different from its progenitor.

The bloom of my new rose is especially noticeable as being a rich golden yellow color, each bloom developing approximately twenty-six petals under normal conditions, and of an unusually large size, and of particularly artistic curvature and configuration, whereby its ensemble is especially attractive.

My new rose differs materially from its parent plant in that it produces longer and more pointed buds; and the central portion of the bloom shows a deeper golden yellow color, gradually assuming a slightly lighter shade of yellow color at its outer parts. Also my rose differs from its parent plant in that it is of much stronger growth; producing longer and stiffer stems; and it is more hardy under adverse climatic conditions. Also it has a more sweet scented and delectable odor, is more vigorous in its growth, and is more prolific in its production of bloom.

It will be understood by rosarians that allowance is to be given in the production of my rose, as the size of the bloom, the color shades, the vigor of the plant, and other features thereof, will vary somewhat on account of differences in the soil, the amount of sunlight and shadow, the amount of humidity in the surrounding atmosphere, and its freedom from insects and disease, which will all contribute materially to slight variations therein.

Having now fully shown and described my new rose, together with its origin, and the manner of its production, what I claim and desire to secure by Letters Patent of the United States, is—

The rose herein shown and described, characterized by the deep rich golden color of the major portion, gradually becoming lighter at its outer portion, its fragrance, long and stiff stems, and the pointed shape and long length of its buds.

EARL H. MANN.